United States Patent [19]

Baidwan et al.

[11] Patent Number: 5,238,003
[45] Date of Patent: Aug. 24, 1993

[54] PLUNGER TIP FOR BLOOD GAS SYRINGE

[76] Inventors: Balinderjeet S. Baidwan; Eva M. Baidwan, both of 1115 Elm St., Denver, Colo. 80220

[21] Appl. No.: 832,718

[22] Filed: Feb. 7, 1992

[51] Int. Cl.⁵ .............................................. A61B 5/00
[52] U.S. Cl. .................................. 128/765; 128/766; 604/190; 604/218; 604/236
[58] Field of Search ............... 604/187, 190, 218, 222, 604/225, 231, 236; 128/760, 763, 764, 765, 766

[56] References Cited

U.S. PATENT DOCUMENTS

| | | | |
|---|---|---|---|
| 4,424,817 | 1/1984 | Williams | 128/766 |
| 4,448,206 | 5/1984 | Martell | 128/765 |
| 4,466,446 | 8/1984 | Baidwan et al. | 128/765 |
| 4,572,210 | 2/1986 | McKinnon | 128/765 |
| 4,632,672 | 12/1986 | Kvitrud | 604/222 |
| 4,690,154 | 9/1987 | Woodford et al. | 128/765 |
| 4,732,162 | 3/1988 | Martell | 128/765 |
| 4,859,336 | 8/1989 | Savas et al. | 210/416.1 |

Primary Examiner—Max Hindenburg
Assistant Examiner—Guy V. Tucker
Attorney, Agent, or Firm—Richard W. Hanes

[57] ABSTRACT

An improved blood drawing syringe characterized by a barrel having a hollow cylindrical bore with an open rear end and a reduced diameter front end for the attachment of a needle, a pushrod disposed for slidable movement within the barrel, a piston attached to the forward end of the pushrod and having a circular disc with spaced apart forward and rear perforated faces enclosing a filter disposed between the faces, a sealing flange disposed around the periphery of the disc sized and dimensioned to fit slidingly within the cylindrical bore of the barrel and a flexible seal abutting the rear face of the disc and adapted to selectively cover the perforations in the rear face of the disc as a function of forward or rearward air pressure on the flexible seal.

5 Claims, 2 Drawing Sheets

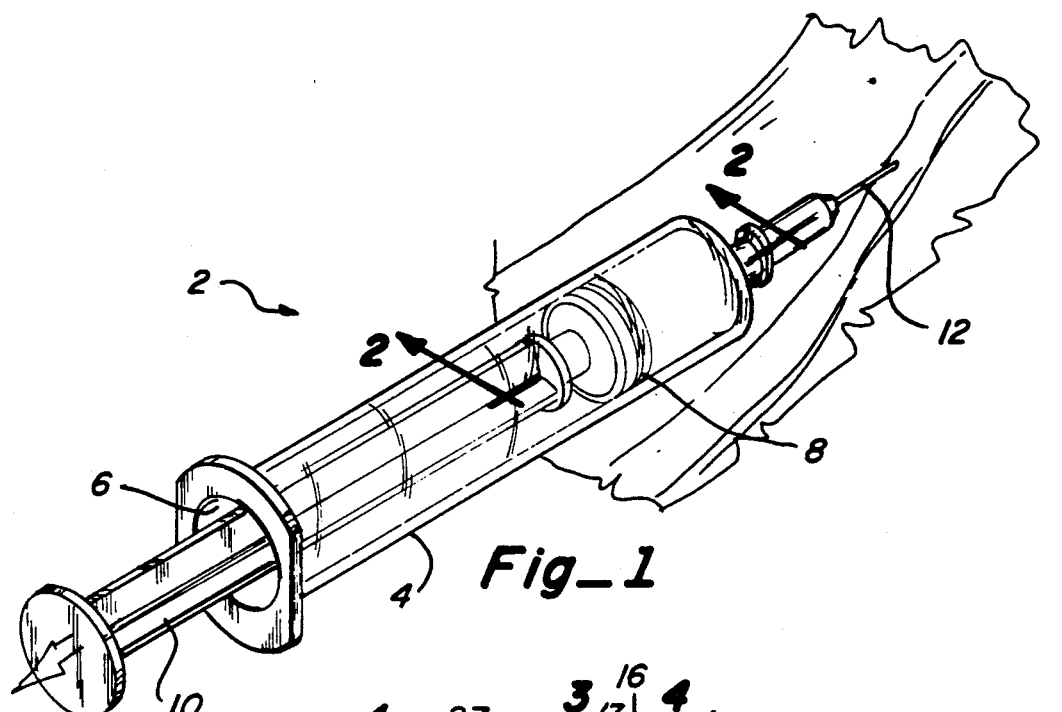
Fig_1
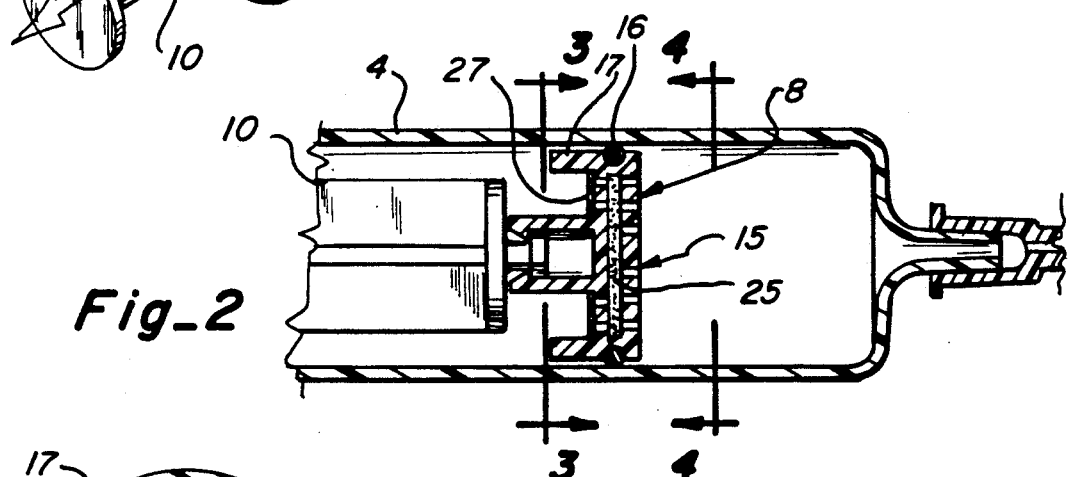
Fig_2
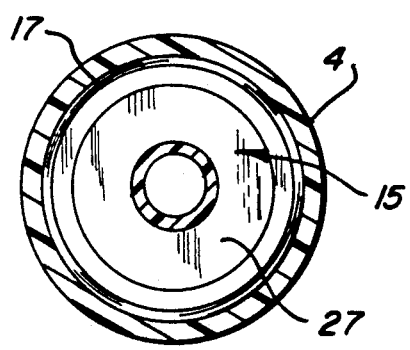
Fig_3
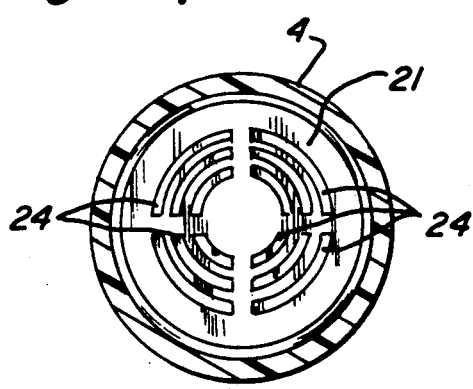
Fig_4

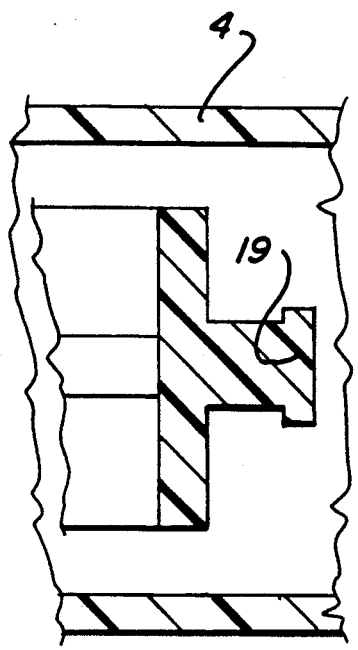
Fig_5
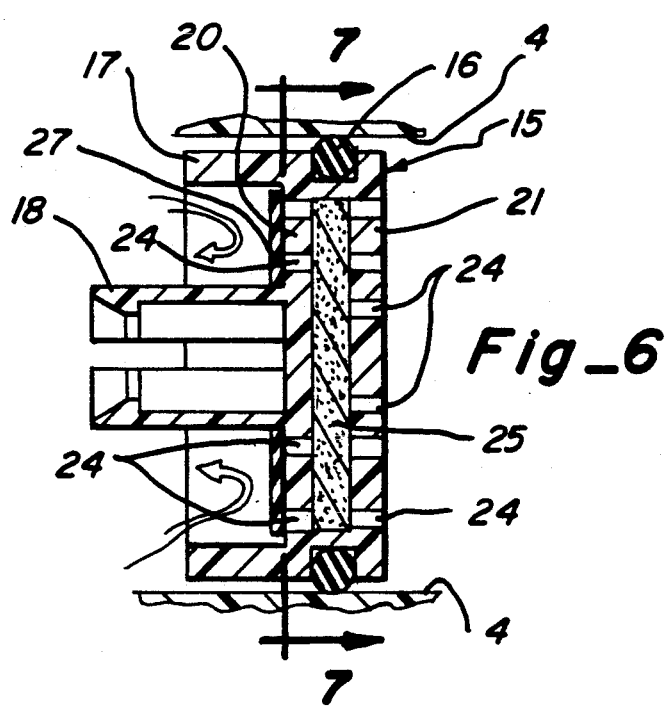
Fig_6
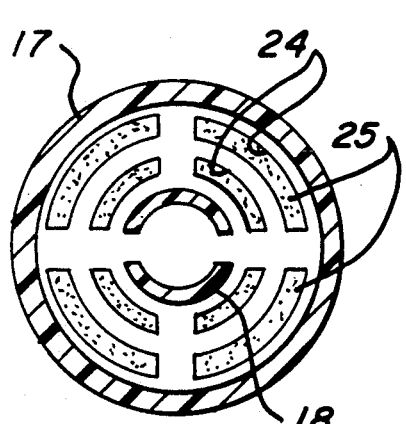
Fig_7
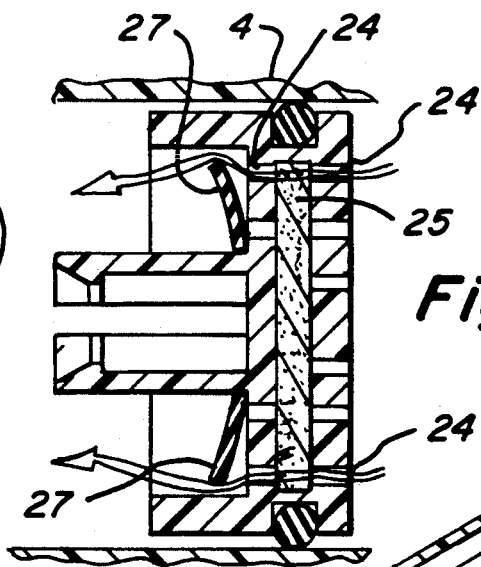
Fig_8
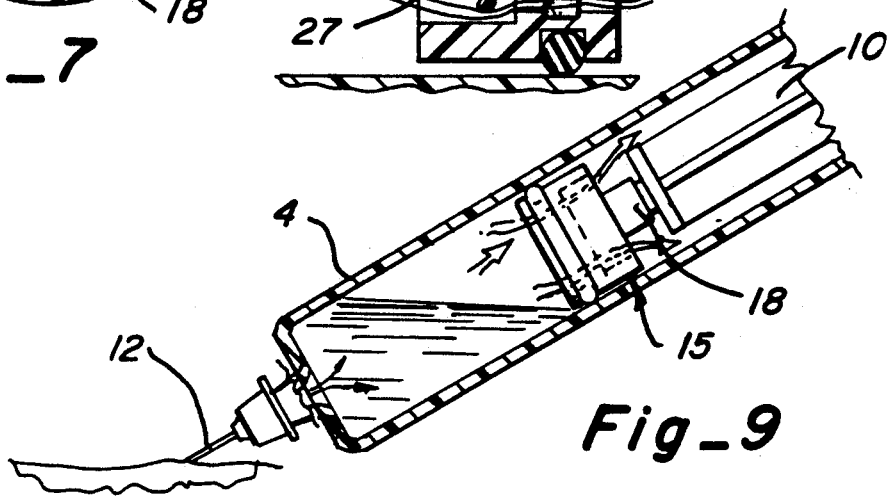
Fig_9

PLUNGER TIP FOR BLOOD GAS SYRINGE

The present invention relates to syringes for drawing blood samples and more particularly to a novel and improved piston for such syringes.

BACKGROUND

Blood drawing syringes comprise a cylindrical barrel having an open rearward end and a reduced diameter front end, or luer, for receiving the mounting collar of a needle. Inside the barrel a piston is movable lengthwise by an attached plunger stem which emerges from the open rear end of the barrel to be grasped by fingers. An example of such a syringe is shown in my U.S. Pat. No. 4,466,446 entitled Plunger Subassembly For Blood Gas Syringes.

To draw blood the plunger stem is first pulled rearwardly to withdraw the piston, providing the necessary volume in the forward end of the barrel for receiving and holding the amount of blood desired to be taken for the sample. The needle mounted on the syringe is then inserted into a blood vessel such as an artery. Arterial blood pressure will usually be sufficient to force the blood through the needle and into the barrel forward of the piston. In some cases, however, there is insufficient blood pressure to fill the barrel and aspiration is necessary in order to produce a low pressure in the forward part of the barrel sufficient to draw the blood. In order to create a lower pressure in the barrel of the syringe than exists in the blood vessel, the piston must be further withdrawn, expanding the volume without admitting air into the space. The prior art has developed two primary types of device to achieve this objective.

The first type employs a hollow or tubular plunger having a filter in its piston through which air can pass from the forward portion of the barrel into the interior of the plunger to be vented through an opening in the rear of the plunger. The filter is of the hydrophobic type which will allow the passage of gases but block the passage of liquid, such as blood. When pushing the plunger into the syringe barrel the open end of the plunger is allowed to remain open to allow the air forward of the piston to escape through the filter and the interior of the plunger tube. When the piston is to be withdrawn with the intent of creating a low pressure aspiration effect, the opening in the plunger must be closed with a thumb or cap in order to block air from moving forwardly through the interior of the plunger tube and through the filter back into the barrel.

If aspiration is found to be necessary after the needle is inserted, positioning a thumb or finger over the opening or locating and positioning the cap or plug to close the open end of the plunger, is awkward at best and difficult to accomplish without painfully gyrating the needle.

A second type of piston arrangement also utilizes a hydrophobic filter, but does not depend on a hollow plunger to convey the air from the forward side of the barrel. Various types of valving arrangements interior of the piston have been worked out but all suffer from one or more difficulties. One type employs a steel ball valve inside the piston, which, if allowed to descend in its channel for a period of time approximating fifteen seconds will seat and act as a block to air flow coming from the rear portion of the piston. The trouble with this arrangement is that the necessity for aspiration must be known in advance of inserting the needle in the blood vessel so that the syringe can be held in a vertical position for the required length of time to seat the ball valve. If the need for aspiration is discovered after needle insertion, normally at 45°, then the needle must first be withdrawn before positioning the syringe vertically to reorient the ball valve.

Another type of plunger tip allows air to pass out of or into the interior of the piston body through slits in the face or perimeter of the piston. Air enters the piston interior through spaces between the head of the plunger and the inside flanges of the piston body against which the head of the plunger bears. Such a system is shown in this inventor's U.S. Pat. No. 4,466,446. It is seen from an examination of the teaching of this patent that when the plunger is pulled out of the barrel the flanged head of the plunger bears tightly against the flanged interior of the piston bore, creating an air tight seal which does not allow air to enter the interior of the piston from the plunger side. Other generally similar syringes are disclosed in U.S. Pat. Nos. 2,882,899; 3,674,181; 3,147,753; 3,164,303; 3,874,382; 3,941,129 and 4,159,713.

The problem which is inherent with syringe pistons of the type disclosed in these patents arises from the very limited degree of aspiration which can be accomplished after needle insertion in cases where the need for aspiration is only then discovered. Normally the piston is positioned for the amount of blood desired to be taken prior to needle insertion. If, however, the blood pressure is sufficient to only partially fill the barrel space or body tissue debris clogs the needle bore and prevents the free flow of blood by arterial pressure, then the plunger must be withdrawn further to provide the necessary low pressure to aspirate the blood into the barrel. But withdrawing the piston from its first position limits the length of the stroke, thereby limiting the low pressure which may be created. In order to maximize the effectiveness of the aspiration the piston should preferably be pushed down in the barrel until it contacts the blood which is in the forward end of the barrel and then withdrawn, creating as large a low pressure as possible. This procedure cannot be done with state of the art pistons because forward movement of the plunger seals the air passage through the piston's interior, forcing the air in the forward part of the tube out through the needle. Pumping air into a blood vessel with this maneuver is not acceptable.

It is therefore the primary object of the present invention to provide a novel blood drawing syringe piston which may be preset in position within the syringe barrel for a given volume of blood to be drawn and which will pass the entrapped air through the piston as blood fills the syringe barrel.

A second object of the invention is to provide a novel blood drawing syringe piston which will accomplish greater aspiration efficiency by permitting the piston to be pushed forward without pumping air through the needle into the blood vessel and permitting the piston to be subsequently withdrawn without admitting air into the enlarging barrel chamber so as to create low pressure therein for aspiration purposes.

BRIEF DESCRIPTION OF THE DRAWINGS

This and other objects, features and advantages of the present invention will become apparent upon a reading of the following detailed description of a preferred form of the invention, taken in conjunction with the accompanying drawings in which:

FIG. 1 is a perspective view of a blood drawing syringe according to the present invention, carrying a needle at its forward end which is inserted into the blood vessel of a limb.

FIG. 2 is a fragmentary longitudinal cross section of the syringe barrel taken along lines 2—2 in FIG. 1.

FIG. 3 is a cross-sectional view of the piston of the present invention taken along lines 3—3 of FIG. 2.

FIG. 4 is a cross-sectional view of the piston of the present invention taken along lines 4—4 of FIG. 2.

FIG. 5 is a fragmentary cross-sectional view of the syringe barrel and the forward attaching end of the interior pushrod.

FIG. 6 is a cross-sectional view of the piston and a fragmentary section of the syringe barrel showing, by the arrows, the air being deflected from the piston flapper seal and prevented from passing forwardly into the barrel ahead of the piston through the piston filter, as the piston is pulled rearwardly (to the left) within the barrel.

FIG. 7 is a cross-sectional view taken along lines 7—7 of FIG. 6.

FIG. 8 is a cross-sectional view similar to that of FIG. 6, but showing, with the arrows, the flow of air through the piston and its filter and around the flapper seal when the piston is pushed forwardly (to the right) within the barrel or when the piston is preset and static and blood is entering the barrel chamber forward of the piston unimpeded under arterial pressure.

FIG. 9 is a fragmentary cross-sectional view of the syringe at approximately a 45 degree angle where the pushrod and piston are static and showing the blood entering the barrel chamber forward of the piston, pushing the entrapped air rearwardly through the piston and its filter and past the flapper seal in the same manner as the air is shown passing through the filter and past the flapper seal in FIG. 8.

SUMMARY OF THE INVENTION

The present invention relates to a novel piston and pushrod assembly for use in a blood drawing syringe characterized by a pushrod having a circular disk attached to its front end where the plane of the disc is perpendicular to the pushrod and the disc has a peripheral flange surmounted by a sealing "O" ring, sized and dimensioned to fit slidingly within the bore of the syringe barrel and where the disc comprises front and rear symmetrically slotted faces which also define an interior space for housing a filter that will pass gases but is impervious to fluids. The assembly further includes a flexible circular flapper seal in abutting contact with the rear face of the disc carried by a mounting nipple on the rear face of the piston.

DETAILED DESCRIPTION

Referring first to FIG. 1, there is shown generally by reference numeral 2 a blood drawing syringe. The syringe includes a tubular barrel 4 having a hollow cylindrical bore and an open rear end 6 to receive the piston 8 and the attached pushrod 10. The front end of the barrel 4 is necked down to detachably receive a needle 12.

The piston 8 is constructed of rigid plastic or similar material and comprises a disc 15 having a peripheral flange 17. Around the outside of the flange is an "O" ring sized and dimensioned to form a sliding seal between the flange 17 and the bore of the barrel. The purpose of the flange is to provide stability to the disc inside the barrel so that the pushrod plunger will remain in alignment with the longitudinal axis of the barrel. The "O" ring seal provides the air and liquid tight seal necessary to prevent air or blood from passing around the periphery of the disc 15.

The disc 15 includes spaced apart front and rear faces 20 and 21 both of which are perforated with holes or slots 24 which are symmetrically placed around the disc and across its diameter. In between the disc faces 20 and 21 is a circular filter 25 that will pass air but is impervious to fluids such as blood. Integral with or attached to the rear face 20 is a projecting split cylindrical tube 18 adapted to receive and hold the flanged end 19 of the pushrod 10 in a manner well known. Carried by the attaching tube 18 and located in abutting contact with the rear face 20 of the disc 15 is a very flexible flat annular flapper seal 27 which is impervious to both gas and fluid.

In operation, the structure described above allows for the normal drawing of blood by positioning the pushrod and disc at the position in the barrel which will create the desired volume in the barrel ahead of the piston to hold the amount of blood desired to be taken. As blood enters the barrel, as shown in FIG. 9, the air in the space being occupied by the blood is pushed out through the slots 24, through the filter 25 and past the deflected flapper seal, as shown in FIGS. 8 and 9. Because the syringe is normally at about a 45° angle, the blood front rises on the front face 21 of the disc, necessitating symmetrical slots 24 over the entire face of the disc so that the escaping air may always have access to an exposed slot or slots. As the air passes upwardly and outwardly through the filter, the air pressure flexes the flapper seal 27 back to allow the air to pass through the slots 24 in the rear face 20 of the disc 15 and around the edges of the flapper seal.

If, after the inserting the needle into the blood vessel, it is discovered that there is insufficient blood pressure to fill the barrel cavity or that the needle has become clogged with body tissue, then the pushrod is moved forwardly in the barrel toward the needle, as shown in FIG. 8, in order to maximize the aspiration stroke which will follow. As the pushrod and piston move forward in the barrel the air which occupies the space forward of the piston will be forced through the slots 24 and the filter 25 and against the flapper 27 similarly to the action described for blood entering the barrel. The flexible nature of the flapper seal 27 will respond to the pressure of the air passing rearwardly through the slots 24 and the filter 25 and flex backwardly, becoming unseated from its normal position of covering the slots 24 in the rear face 20 of the disc 15 and allowing the air to pass freely through the disc and out the rear opening of the syringe barrel 4.

With the front face 21 of the disc 15 positioned at the blood front in the barrel 4 the rearward aspiration stroke can begin in order to lower the pressure ahead of the piston 8 and draw the blood into the barrel 4. When the pushrod is withdrawn from its most forward position the air in the barrel rearwardly of the piston would have a normal tendency to pass back through the disc and the filter and to again fill the volume of space being created ahead of the piston by the withdrawal of the pushrod. This passage of air is prevented however by the flapper seal 27 which, by reverse air pressure, is seated firmly against the back face 21 of the disc 15 to seal the slots 24 and prevent air from passing through the disc and filter, as shown in FIG. 6.

The action of the flapper seal at the rear face 20 of the disc 15 accomplishes all of the objectives of the invention by allowing the piston 8 to be longitudinally moved within the barrel of the syringe while the needle is inserted in the blood vessel without the danger of forcing air into the blood vessel but at the same time being able to create the maximum aspiration stroke to most effectively draw the blood from a low pressure vessel or an obstructed needle.

We claim:

1. A fluid drawing syringe comprising,
   a barrel having a hollow cylindrical bore with an open rear end and a reduced diameter front end for the attachment of a needle,
   a pushrod having a forward end and disposed for slidable movement within the barrel,
   piston means attached to the forward end of the pushrod and comprising,
   circular disc means having spaced apart forward and rear perforated faces,
   each perforated face having a plurality of perforations arranged in its face,
   filter means disposed between said forward perforated face and said rear perforated face to cover the perforations of said faces,
   sealing means disposed between the periphery of the disc means and the cylindrical bore of the barrel, and
   a flexible seal movable in response to air pressure in said barrel abutting the rear face of the disc means, said flexible seal movable from a first position to cover the perforations in said rear face to a second position to uncover said perforations in said rear face.

2. The apparatus of claim 1 wherein the perforations in the forward and rear faces of the disc means are symmetrical about the center axis of the disc means and extend across the front and rear faces of the disc means.

3. The apparatus of claim 1 wherein the filter means is hydrophobic.

4. The apparatus of claim 1 wherein the sealing means includes an "O" ring surmounted on the disc means for making sealing contact with the inside of the said cylindrical bore of the barrel.

5. The apparatus of claim 1 where the disc means includes a stabilizing flange around the periphery thereof.

* * * * *